(12) United States Patent
Silverman et al.

(10) Patent No.: US 6,919,298 B2
(45) Date of Patent: Jul. 19, 2005

(54) ENHANCED HERBICIDE COMPOSITION

(75) Inventors: F. Paul Silverman, Highland Park, IL (US); Peter D. Petracek, Grayslake, IL (US); Zhiguo Ju, Shangdong (CN); Daniel F. Heiman, Libertyville, IL (US); Prem Warrior, Green Oaks, IL (US)

(73) Assignee: Valent Biosciences Corporation, Libertyville, IL (US)

( * ) Notice: Subject to any disclaimer, the term of this patent is extended or adjusted under 35 U.S.C. 154(b) by 166 days.

(21) Appl. No.: 10/324,980

(22) Filed: Dec. 19, 2002

(65) Prior Publication Data

US 2004/0009876 A1 Jan. 15, 2004

Related U.S. Application Data

(60) Provisional application No. 60/421,715, filed on Oct. 28, 2002, provisional application No. 60/407,456, filed on Aug. 30, 2002, and provisional application No. 60/369,926, filed on Apr. 4, 2002.

(51) Int. Cl.$^7$ ........................ A01N 25/32; A01N 33/12; A01N 43/40; A01N 43/60
(52) U.S. Cl. ...................... 504/130; 504/137; 504/138; 504/139
(58) Field of Search ................................. 504/130, 137, 504/138, 139

(56) References Cited

U.S. PATENT DOCUMENTS

| | | |
|---|---|---|
| 4,931,581 A | 6/1990 | Schurter et al. |
| 5,015,649 A | 5/1991 | Kunz |
| 6,218,336 B1 | 4/2001 | Coleman |
| 2002/0004457 A1 | 1/2002 | Nevill et al. |
| 2002/0035738 A1 | 3/2002 | Thomma et al. |

OTHER PUBLICATIONS

Ryals et al. << Systemic Acquired Resistance >>. The Plant Cell. vol. 8. p. 1809–1819, 1996.*
Devine et al. Physiology of Herbicide Action. NJ:PTR Prentice Hall. P. 163–166. 1993.*
European Commission, 17$^{th}$ International Conference on Plant Growth Substances, Brno, Czech Republic Jul. 1–6, 2001.

NIAES—Division of Pesticides, Annual Report 1997.

Pesticides: Regulating Pesticides, U.S. Enviromental Protection Agency; Harpin Protein (006477).

R.F. Van Toor et al.; Evaluation of Acibenzolar–S–Methyl for Induction of Resistance in Carmellia Flowers to *Ciborinia camelliae* Infection; New Zealand Plant Protection 54:209–212(2001).

E. Antonova Ananieva et al.; Treatment with salicylic acid decreases the effects of paraquat on photosynthesis; J. Plant Physiol. 159:685–693 (2002).

Lowell Klepper; Synergistic Levels of NoxEmissions from soybean Leaves Caused by a Combination of Salicylic Acid and Photosynthetic Inhibitor Herbicides; Pesticide Biochemistry and Physiology 32, 173–179 (1988).

N.E. Strobel et al.; Chemical and Biological Inducers of Systemic Resistance to Pathogens Protect Cucumber and Tobacco Plants from Damage Caused by Paraquat and Cupric Chloride; University of Kentucky; Journal paper 95–12–081 ; Accepted for publication Aug. 22, 1995.

M.V. Rao et al.; Influence of Salicyclic Acid on H2O2 Production, Oxidative Stress, and H2O2 Production, Oxidative Stress, and H2O2–Metabolizing Enzymes; Plant Physiol. (1997) 115:137–149.

Oliver C. Knorzer et al.; Antagonizing Peroxidizing Herbicides; Springer–Verlag Berlin Heidelberg 1999.

* cited by examiner

*Primary Examiner*—S. Mark Clardy
(74) *Attorney, Agent, or Firm*—Wood, Phillips, Katz, Clark & Mortimer

(57) ABSTRACT

An herbicide composition comprising a PSI inhibitor and a salicylate or another SAR inducer and methods of use for said composition is disclosed.

15 Claims, No Drawings

ENHANCED HERBICIDE COMPOSITION

This application claims benefit of provisional applications 60/369,926, filed Apr. 4, 2002; 60/407,456, filed Aug. 30, 2002; and 60/421,715, filed Oct. 28, 2002.

BACKGROUND OF THE INVENTION

A variety of herbicides have been used to kill unwanted plants (weeds) in crop fields or orchards. Typically, these herbicides are sprayed onto the soil (pre-emergence) or onto the plants (post-emergence).

Herbicides are expensive, and their use may result in unintended consequences such as groundwater contamination, crop damage, environmental damage, spray drift, and human and mammalian health concerns.

There are many classes of herbicides that may be grouped based on their mode of action. One class of herbicides of particular interest are the bipyridylium salts. These compounds inhibit photosystem I (PSI) and are exemplified by paraquat and diquat. Paraquat is marketed under many names in the US including Gramoxone® and Gramoxone Extra®, while diquat is marketed under several names including Reglone® and Reglox®. Bipyridylium salts act by diverting electrons from PSI of photosynthesis and are subsequently reduced by molecular oxygen. This results in the generation of superoxides and related free-radical species. The cellular damage resulting from free-radical oxidation kills the plant.

There are many compounds that may be classified as inducers of plant systemically acquired resistance (SAR). Although these compounds fall into many structural classes, all of these compounds or mixtures of compounds are able to increase the resistance of plants to pathogen attack. Many of these SAR inducers cause changes in the salicylate-dependent pathway of resistance (ie. Harpin), others may mimic salicylate (ie BTH), or others may induce resistance through ethylene and jasmonate dependent pathways (ie ethephon).

It is an object of the present invention to safen crop plants from unintended herbicidal consequences of paraquat and diquat application. It is also an object of this invention to lessen the effects of spray drift on non-target species when these herbicides are used.

SUMMARY OF THE INVENTION

The present invention is directed to a composition comprising an herbicide and a salicylate or another inducer of systemic acquired resistance (SAR inducer). In particular, herbicide compositions comprising a PSI inhibitor and a salicylate or another SAR inducer are shown.

The present invention is also directed to a method of altering the herbicidal activity of an herbicide with the presence of a salicylate or another SAR inducer. In particular, the present invention is directed to a method of altering the herbicidal activity of a bipyridylium salt comprising adding to the bipyridylium salt an effective amount of a salicylate or another SAR inducer. More particularly, the present invention is directed to a method of safening a crop plant against the herbicidal activity of a PSI inhibitor comprising adding to the PSI inhibitor an effective amount of an SAR inducer.

In another embodiment, the present invention relates to a method of increasing the selectivity of a PSI inhibitor comprising adding to the PSI inhibitor an effective amount of a salicylate or another SAR inducer.

A further embodiment of the present invention is also directed to a method of altering the herbicidal activity of an herbicide with the presence of a salicylate or another SAR inducer. In particular, the present invention is directed to a method of altering the herbicidal activity of a PSI inhibiting herbicide comprising adding to said PSI inhibiting herbicide an effective amount of a salicylate or another SAR inducer.

DETAILED DESCRIPTION OF THE INVENTION

As used herein, an "SAR" inducer is defined as any compound which has the ability to turn on resistance in a plant to a disease-causing agent, including, but not limited to a virus, a bacterium, a fungus, or combinations of these agents. In addition, an SAR inducer may induce resistance to insect feeding in a plant, as defined by Enyedi et al. (1992; Cell 70: 879–886).

Exemplary SAR inducers cover many structural families of compounds, but are united by their ability to induce a resistance to plant diseases and pest feeding. One class of SAR inducers is the salicylates. The commercial SAR inducers Actigard™, Messenger™, Keyplex® 350-DP®, and Oryzemate are useful in the present invention. Elicitors, including the Goemar products are another class of experimental SAR inducers that may have utility for this use. In addition, ethylene, its biosynthetic precursors, or ethylene releasing compounds such as Ethrel are considered SAR inducers of utility in this context. In addition, other compounds which share the common stimulation of disease resistance pathways in plants are inducers of systemic acquired resistance, and may be used for safening plants from PSI inhibitors, such as paraquat.

As used herein, "salicylate" is defined as any substituted or unsubstituted benzoic acid having a hydroxyl group in the 2- or ortho-position, or a biologically acceptable salt or biological or chemical precursor thereof. Substitution on the benzoic acid includes mono-, di-, tri- or tetra-substitution in the 3-, 4-, 5- and/or 6-positions: substituents may be chosen in any combination from: lower alkyl groups of 1 to 4 carbons; an alkyl bridge containing 3 or 4 carbons attached to the benzoic acid at two adjacent points; lower alkoxy groups of from 1 to 4 carbons; the halogens fluorine, chlorine, bromine or iodine; an amino group, wherein the nitrogen may carry 0, 1, or 2 identical or different lower alkyl groups of from 1 to 4 carbons each; the nitro group; the formyl group; the acetyl group; the hydroxymethyl group; the methoxycarbonyl group; the carboxamido or sulfonamido groups wherein the nitrogen may carry 0, 1 or 2 identical or different lower alkyl substituents of from 1 to 4 carbons each; the cyano group; an alkylthio-, alkylsulfoxy- or alkylsulfonyl group, wherein the alkyl group is comprised of from 1 to 4 carbons; or a mono-, di- or trifluoromethyl group. Biologically acceptable salts include those of the common alkali metals sodium and potassium, the alkaline earths magnesium or calcium, zinc, or ammonium or simple alkylammonium cations such as mono-, di-, tri- or tetramethylammonium or other ammonium cations bearing up to 7 carbons. Biological or chemical precursors of 2-hydroxylated benzoic acid include non-hydroxylated benzoic acid and derivatives thereof having at least one ortho-position free, wherein the hydroxyl group is introduced biologically by the natural metabolic processes of the plant to which it is applied. Biological or chemical precursors of 2-hydroxylated benzoic acid also include benzoic acid compounds wherein the hydroxyl group in the 2-position is masked chemically in such a way that the masking group is labile and is easily removed once the compound has been applied to a plant, either by an enzymatic process of the plant's normal metabolism or by slow spontaneous hydrolysis. Examples of such masking groups include esters with monocarboxylic acids of from 1 to 7 carbons and trialkylsilyl ethers containing from 3 to 13 carbons. Furthermore, the term "salicylate" as used herein is understood to include mixtures of two or more of the individual pure substances defined above.

The compositions of the present invention contain from 99.999% to 0.001% PSI inhibitor and from 99.999% to 0.001% salicylate or another SAR inducer, preferably from 99.99.0% to 0.005% PSI inhibitor and from 99.99% to 0.005% salicylate or another SAR inducer and most preferably from 99.9% to 0.01% PSI inhibitor and from 99.9% to 0.01% salicylate or another SAR inducer with the remainder of the composition being water or another inert solvent.

The compositions of the present invention may also be formulated as an aqueous herbicidal concentrate which is sufficiently storage stable for commercial use and which is diluted with water before use. Such concentrates have a concentration of from 100% to 0.01% of the herbicidal compositions of the present invention, preferably 50% to 0.1% and most preferably 30% to 1%.

The compositions of the present invention are dispersed or dissolved in water to a concentration of from 15% to 0.0015%, preferably 5.0% to 0.002% and most preferably 0.6% to 0.05% for application.

In an alternative embodiment of the present invention, the PPO inhibitor may be formulated as a concentrate and salicylate or another SAR inducer or a combination thereof may be formulated as a concentrate. The two concentrates are then mixed and diluted prior to use.

Representative PSI inhibitors useful in the present invention are paraquat (methyl viologen; 1,1'-dimethyl-4,4'-bipyridinium ion; CAS registry no. 4685-14-7), diquat(1,1'-ethylene-2,2'-bipyridyidiylium ion; CAS registry no. 2764-72-9) and their salts. Bipyridylium herbicides include Gramoxone® and Reglone® and any formulation containing paraquat or diquat or their salts alone or in combination with other herbicides.

Representative SAR inducers useful in the present invention include Actigard™ (Benzo(1,2,3)thiadiazole-7-carbothioic acid-S-methyl ester), Syngenta Crop Protection, Greensboro, N.C.; Messenger™ (Harpin protein, a naturally occurring bacterial protein), Eden Bioscience, Bothel, Wash.; Keyplex® 350-DP®, Morse Enterprises Ltd., Miami, Fla.; and Florel® brand Ethephon, Southern Agricultural Insecticides, Palmetto, Fla.

Compositions of the present invention include both solid and liquid compositions, which are ready for immediate use, and concentrated compositions, which require dilution before use, usually with water.

The solid compositions may be in the form of granules, or dusting powders wherein the active ingredient is mixed with a finely divided solid diluent (e.g. kaolin, bentonite, kieselguhr, dolomite, calcium carbonate, talc, powdered magnesia, Fuller's earth or gypsum). They may also be in the form of dispersible powders of grains, comprising a wetting agent to facilitate the dispersion of the powder or grains in liquid. Solid compositions in the form of a powder may be applied as foliar dusts.

Liquid compositions may comprise a solution, suspension or dispersion of the active ingredients in water or a water-miscible organic solvent, optionally containing a surface-active agent, or may comprise a solution or dispersion of the active ingredient in a water immiscible organic solvent which is dispersed as droplets in water. Preferred active ingredients of the composition of the present invention are water-soluble herbicides or are readily suspended in water and it is preferred to use aqueous compositions and concentrates.

The compositions of the present invention may contain additional surface-active agents, including for example surface-active agents to increase the compatibility or stability of concentrated compositions as discussed above. Such surface-active agents may be of the cationic, anionic, or non-ionic or amphoteric type or mixtures thereof. The cationic agents are, for example, quaternary ammonium compounds (e.g. cetyltrimethylammonium bromide). Suitable anionic agents are soaps, salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble of dispersible surface active agents having a skeleton which comprises a siloxane chain e.g. Silwet L77®). A suitable mixture in mineral oil is ATPLUS 411F®.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carrier such as ammonium nitrate, urea, and the like.

The rate of application of the compositions of the present invention will depend on a number of factors including, for example, the active ingredients, the plant species whose growth is to be safened, the growth stage of the plant, the formulation and the method of application, as for example, spraying, addition to irrigation water or other conventional means. As a general guide, however, the application rate of spray solution is from 1000 to 10 liters per hectare, preferably from 250 to 100 liters per hectare.

Representative plant species that may be treated with the compositions of the present invention include *Nicotiana tabacum* (tobacco), and *Chenopodium album* (lambsquarter) but it is not intended that the use of the compositions and methods of this invention be limited only to those species.

The present invention may be illustrated by the following representative examples:

EXAMPLES

In all experiments, deionized ultra-pure water was used in preparing solutions. Spray solutions were used as soon as possible after mixing.

The herbicides and spray adjuvants used in these studies included: crop oil concentrate (COC; Orchex 796, 83%; Ag Plus300F® 17%), the bipyridylium salts methyl viologen (paraquat) or diquat, sodium salicylate (Na SA) and the SAR inducers Actigard, Messenger, Keyplex 350-DP, and Florel.

In all herbicide applications, plants were sprayed with a sufficient volume to insure full coverage, and resulted in runoff of the spray solution. COC was added to all spray solutions at a rate of 0.25% (v/v). For all treatments containing both an herbicide and an SAR inducer, these materials were mixed and applied in a single spray solution (commonly known as a tank mix). After spraying, plants were moved to the greenhouse and arranged in a randomized complete block experimental design. Plants were evaluated for phytotoxicity/herbicidal effects after spraying by assessing damage according to percent leaf area affected.

All the data were subject to an analysis of variance, and the mean separations were determined with Duncan's new multiple range test at $\alpha=0.05$. The present invention may be illustrated by the following representative examples:

Example 1

The addition of salicylate to the spray solution safened the plants from paraquat herbicide damage on tobacco (Table 1). The effect was observed at all rates of paraquat tested, and persisted through the course of the experiment.

TABLE 1

Effect of sodium salicylate (NaSA) on paraquat herbicidal activity against tobacco

| Treatment | Phytotoxicity at 4d | Phytotoxicity at 6d |
|---|---|---|
| Crop Oil Concentrate, 0.25% (v/v) | 1.0 A | 1.0 A |
| NaSA, 10 mM + COC 0.25% | 1.3 AB | 1.2 ABC |
| Paraquat 75 mg/l + COC 0.25% | 3.8 E | 3.7 E |
| Paraquat 75 mg/l + 10 mM NaSA + COC 0.25% | 1.6 BC | 1.6 BC |
| Paraquat 37.5 mg/l + COC 0.25% | 2.9 D | 2.7 D |
| Paraquat 37.5 mg/l + 10 mM NaSA + COC 0.25% | 1.3 AB | 1.3 ABC |
| Paraquat 7.5 mg/l + COC 0.25% | 1.9 C | 1.6 C |
| Paraquat 7.5 mg/l + 10 mM NaSA + COC 0.25% | 1.2 AB | 1.1 AB |

Phytotoxicity rating: 1 = no damage, 2 = 25% leaf area damaged, 3 = 50% leaf area damaged, 4 = 75% leaf area damaged, 5 = 100% leaf area damaged (dead).
n = 5 plants. Mean separation by Duncan's New Multiple Range Test ($\alpha$ = 0.05).

Example 2

The ability of salicylate to protect plants from Paraquat damage was not limited to tobacco and dicotyledonous plants. Table 2 demonstrates that the ability of salicylate to safen plants from paraquat damage on a monocotyledonous plant species.

TABLE 2

Effect of sodium salicylate (NaSA) on paraquat herbicidal activity against giant foxtail

| Treatment | Phytotoxicity at 3d | Phytotoxicity at 7d | Phytotoxicity at 10d | Phytotoxicity at 14d |
|---|---|---|---|---|
| Crop Oil Concentrate, 0.25% (v/v) | 1.0 A | 1.0 A | 1.0 A | 1.0 A |
| NaSA, 10 mM + COC 0.25% | 1.0 A | 1.0 A | 1.0 A | 1.0 A |
| Paraquat 75 mg/l + COC 0.25% | 4.3 D | 4.7 D | 4.7 D | 4.7 C |
| Paraquat 75 mg/l + 10 mM NaSA + COC 0.25% | 1.7 B | 1.9 B | 1.8 B | 1.6 A |
| Paraquat 37.5 mg/l + COC 0.25% | 3.4 C | 4.0 C | 4.1 C | 3.9 B |
| Paraquat 37.5 mg/l + 10 mM NaSA + COC 0.25% | 1.4 AB | 1.4 AB | 1.3 AB | 1.2 AB |
| Paraquat 7.5 mg/l + COC 0.25% | 1.6 B | 1.6 B | 1.4 AB | 1.3 A |
| Paraquat 7.5 mg/l + 10 mM NaSA + COC 0.25% | 1.0 A | 1.0 A | 1.0 A | 1.0 A |

Phytotoxicity rating: 1 = no damage, 2 = 25% leaf area damaged, 3 = 50% leaf area damaged, 4 = 75% leaf area damaged, 5 = 100% leaf area damaged (dead).
n = 5 plants. Mean separation by Duncan's New Multiple Range Test ($\alpha$ = 0.05).

Example 3

The ability of salicylate to safen plants from paraquat damage is not limited to paraquat alone. SA is also able to safen tobacco against the herbicide diquat (Table 3), demonstrating that the effect is more generalized within this class of herbicides.

TABLE 3

Effect of sodium salicylate (NaSA) on paraquat or diquat herbicidal activity against tobacco

| Treatment | Phytotoxicity at 1d | Phytotoxicity at 4d | Phytotoxicity at 6d | Phytotoxicity at 12d |
|---|---|---|---|---|
| Crop Oil Concentrate, 0.25% (v/v) | 1.0 A | 1.0 A | 1.0 A | 1.0 A |
| NaSA, 10 mM + COC 0.25% | 1.3 AB | 1.1 A | 1.1 A | 1.2 A |
| Paraquat 150 mg/l + COC 0.25% | 4.1 E | 4.5 C | 4.7 C | 4.2 C |
| Paraquat 150 mg/l + 10 mM NaSA +COC 0.25% | 1.8 BC | 2.0 B | 2.0 B | 2.2 B |
| Diquat 150 mg/l + COC 0.25% | 3.3. D | 4.3 C | 4.3 C | 3.9 C |
| Diquat 150 mg/l + 10 mM NaSA + COC 0.25% | 2.0 C | 2.5 B | 2.5 B | 2.2 B |

Phytotoxicity rating: 1 = no damage, 2 = 25% leaf area damaged, 3 = 50% leaf area damaged, 4 = 75% leaf area damaged, 5 = 100% leaf area damaged (dead).
n = 5 plants. Mean separation by Duncan's New Multiple Range Test ($\alpha$ = 0.05).

Example 4

Salicylate protection against paraquat damage is not only dependent on the presence of sodium salicylate in the spray solution. When salicylate was applied through hydroponic pre-treatment prior to application of paraquat, significant protection from paraquat damage resulted (Table 4).

TABLE 4

Effect of sodium salicylate (NaSA) hydroponic pretreatment for 24 h on paraquat herbicidal activity against tobacco

| Hydroponic pre-treatment for 24 hours | Spray treatment | Phytotoxicity at 1d post-spraying | Phytotoxicity at 4d post-spraying | Phytotoxicity at 6d post-spraying |
|---|---|---|---|---|
| Water | Crop Oil Concentrate 0.25% | 1.0 A | 1.0 A | 1.0 A |
| Water | Paraquat 150 mg/l + COC 0.25% | 3.7 D | 3.8 D | 3.4 E |
| NaSA, 1.0 mM | Paraquat 150 mg/l + COC 0.25% | 2.3 C | 3.2 C | 3.0 E |
| NaSA, 10 mM | Paraquat 150 mg/l + COC 0.25% | 1.6 B | 2.0 B | 2.2 D |

TABLE 4-continued

Effect of sodium salicylate (NaSA) hydroponic pretreatment for 24 h on paraquat herbicidal activity against tobacco

| Treatments | | Phyto-toxicity at 1d post-spraying | Phyto-toxicity at 4d post-spraying | Phyto-toxicity at 6d post-spraying |
|---|---|---|---|---|
| Hydroponic pre-treatment for 24 hours | Spray treatment | | | |
| NaSA, 50 mM | Paraquat 150 mg/l + COC 0.25% | 1.5 AB | 1.8 B | 2.1 D |
| NaSA, 1.0 mM | Crop Oil Concentrate 0.25% | 1.0 A | 1.0 A | 1.1 AB |
| NaSA, 10 mM | Crop Oil Concentrate 0.25% | 1.0 A | 1.0 A | 1.3 ABC |
| NaSA, 50 mM | Crop Oil Concentrate 0.25% | 1.2 AB | 1.5 AB | 1.7 BCD |
| Water | NaSA, 10 mM + COC 0.25% | 1.4 AB | 1.4 AB | 1.3 ABC |
| Water | Paraquat 150 mg/l + 10 mM NaSA + COC 0.25% | 1.5 AB | 1.7 B | 1.8 CD |

Phytotoxicity rating: 1 = no damage, 2 = 25% leaf area damaged, 3 = 50% leaf area damaged, 4 = 75% leaf area damaged, 5 = 100% leaf area damaged (dead).
n = 4 plants. Mean separation by Duncan's New Multiple Range Test ($\alpha$ = 0.05).

Moreover, application of sodium salicylate as a spray solution prior to application of paraquat also resulted in safening (Table 5). In this experiment, the plants were treated and kept in the dark for 48 hours from the first spray treatment to delay the light-dependent effects of paraquat.

TABLE 5

Effect of dark pretreatment with sodium salicylate (NaSA) on paraquat herbicidal activity against tobacco

| Treatments | | | Phytotoxicity after 3 days in the light (5 days after initial spray) | Phytotoxicity after 12 days in the light (14 days after initial spray) |
|---|---|---|---|---|
| Treatment Number | Spray treatment at 0 hours | Spray treatment at 24 hours | | |
| 1 | Crop Oil Concentrate 0.25% | | 1.0 A | 1.0 A |
| 2 | Paraquat 150 mg/l + COC 0.25% | | 5.0 D | 5.0 D |
| 3 | Paraquat 150 mg/l + 10 mM NaSA + COC 0.25% | | 2.6 C | 2.5 C |
| 4 | NaSA, 10 mM + COC 0.25% | | 1.4 B | 1.5 B |
| 5 | NaSA, 10 mM + COC 0.25% | Paraquat 150 mg/l + COC 0.25% | 2.6 C | 2.3 C |

For treatments 1 to 4, plants were sprayed at 0 hours, held in the dark for 48 hours, and moved into the light. For treatment 5, plants were sprayed with NaSA at 0 hours, held in the dark for 24 hours, sprayed with paraquat, and held in the dark for an additional 24 hours before being moved into the light.
Phytotoxicity rating: 1 = no damage, 2 = 25% leaf area damaged, 3 = 50% leaf area damaged, 4 = 75% leaf area damaged, 5 = 100% leaf area damaged (dead). n = 4 plants. Mean separation by Duncan's New Multiple Range Test ($\alpha$ = 0.05).

Example 5

The ability of salicylate to protect plants from paraquat damage was not limited to sodium salicylate, but is also seen with other salicylate derivatives on tobacco. For example, 5-fluorosalicylate is able to safen tobacco from paraquat (Table 6).

TABLE 6

Effect of sodium salicylate (NaSA) or 5-fluorosalicylate (5-FSA) on paraquat herbicidal activity against tobacco

| Treatment | Phyto-toxicity at 6d | Phyto-toxicity at 8d | Phyto-toxicity at 11d |
|---|---|---|---|
| Crop Oil Concentrate, 0.25% (v/v) | 1.0 A | 1.0 A | 1.0 A |
| NaSA, 10 mM + COC 0.25% | 1.1 A | 1.1 A | 1.1 A |
| 5-FSA, 5 mM + COC 0.25% | 2.3 B | 2.8 B | 2.0 B |
| Paraquat 150 mg/l + COC 0.25% | 5.0 E | 5.0 C | 5.0 E |
| Paraquat 150 mg/l + 10 mM NaSA + COC 0.25% | 2.8 C | 3.1 B | 2.4 C |
| Paraquat 150 mg/l + 5 mM 5-FSA + COC 0.25% | 4.4 D | 4.8 C | 4.6 D |

Phytotoxicity rating: 1 = no damage, 2 = 25% leaf area damaged, 3 = 50% leaf area damaged, 4 = 75% leaf area damaged, 5 = 100% leaf area damaged (dead).
n = 3 plants. Mean separation by Duncan's New Multiple Range Test ($\alpha$ = 0.05).

Example 6

The ability of sodium salicylate to safen plant species is not observed in all species. Several of the weed species tested, such as lambsquarters, showed limited or no protection from paraquat damage when sodium salicylate was applied (Table 7).

TABLE 7

Effect of sodium salicylate (NaSA) on paraquat herbicidal activity against lambsquarter (*Chenopodium album*)

| Treatment | Phyto-toxicity at 2d | Phyto-toxicity at 4d | Phyto-toxicity at 7d |
|---|---|---|---|
| Crop Oil Concentrate, 0.25% (v/v) | 1.0 A | 1.0 A | 1 A |
| NaSA, 10 mM + COC 0.25% | 1.7 AB | 1.65 A | 1.4 A |
| Paraquat 150 mg/l + COC 0.25% | 3.9 C | 3.9 BC | 3.9 BC |
| Paraquat 150 mg/l + 10 mM NaSA + COC 0.25% | 3.9 C | 4.2 C | 4.4 C |

Phytotoxicity rating: 1 = no damage, 2 = 25% leaf area damaged, 3 = 50% leaf area damaged, 4 = 75% leaf area damaged, 5 = 100% leaf area damaged (dead).
n = 5 plants. Mean separation by Duncan's New Multiple Range Test ($\alpha$ = 0.05).

The utility of using a salicylate to safen a crop plant to paraquat or other bipyridylium salt herbicide (PSI inhibitor) utilizes the differential safening shown in Table 7.

Example 7

The addition of the SAR inducer Actigard (BTH) to the spray solution safened the plants from paraquat herbicide damage on tobacco (Table 8). The effect was observed at both rates of BTH tested, and persisted through the course of the experiment.

TABLE 8

Effect of Actigard (BTH) on paraquat herbicidal activity against tobacco

| Treatment | Phytotoxicity at 2d: Percent Leaf Area Affected | Phytotoxicity at 4d: Percent Leaf Area Affected | Phytotoxicity at 7d: Percent Leaf Area Affected |
|---|---|---|---|
| Crop Oil Concentrate, 0.25% (v/v) | 0 A | 0 A | 0 A |
| NaSA 1600 mg/l + COC 0.25% | 11.3 B | 7.5 AB | 5 AB |
| Actigard 187 mg/l + COC 0.25% | 0 A | 0 A | 0 A |
| Actigard 935 mg/l + COC 0.25% | 1 A | 0 A | 0 A |
| Paraquat 150 mg/l + COC 0.25% | 61.25 E | 62.5 F | 50 D |
| Paraquat 150 mg/l + NaSA 1600 mg/l + COC 0.25% | 12.5 B | 12.5 BC | 7.5 AB |
| Paraquat 150 mg/l + Actigard 187 mg/l + COC 0.25% | 25 CD | 20 DE | 15 BC |
| Paraquat 150 mg/l + Actigard 935 mg/l + COC 0.25% | 22.5 C | 17.5 CD | 12.5 B | n = 5 plants. Mean separation by Duncan's New Multiple Range Test (α = 0.05).

Example 8

The addition of the SAR inducer Messenger (Harpin) to the spray solution safened the plants from paraquat herbicide damage on tobacco (Table 9). The effect was observed at both rates of Harpin tested, and persisted through the course of the experiment. This table demonstrates that the observed affect is not limited to the BTH, which is a synthetic mimic of salicylate.

TABLE 9

Effect of Messenger (Harpin) on paraquat herbicidal activity against tobacco

| Treatment | Phytotoxicity at 2d: Percent Leaf Area Affected | Phytotoxicity at 5d: Percent Leaf Area Affected |
|---|---|---|
| Crop Oil Concentrate, 0.25% (v/v) | 0 A | 0 A |
| NaSA 1600 mg/l + COC 0.25% | 3.25 A | 3.25 A |
| Messenger 1120 mg/l + COC 0.25% | 0 A | 0 A |
| Messenger 11220 mg/l + COC 0.25% | 0 A | 0 A |
| Paraquat 187 mg/l + COC 0.25% | 65 E | 83.75 E |
| Paraquat 187 mg/l + NaSA 1600 mg/l + COC 0.25% | 15 B | 23.75 B |
| Paraquat 187 mg/l + Messenger 1120 mg/l + COC 0.25% | 50 D | 71.25 D |
| Paraquat 187 mg/l + Messenger 11200 mg/l + COC 0.25% | 30 C | 52.5 C | n = 5 plants. Mean separation by Duncan's New Multiple Range Test (α = 0.05).

Example 9

The addition of the SAR inducer Keyplex 350-DP to the spray solution safened the plants from paraquat herbicide damage on tobacco (Table 10). The effect was observed at both rates of Keyplex tested, and persisted through the course of the experiment. This table demonstrates that the observed effect is not limited to known SAR inducers, as the MOA of Keyplex is not clearly understood.

TABLE 10

Effect of Keyplex 350-DP on paraquat herbicidal activity against tobacco

| Treatment | Phytotoxicity at 1d: Percent Leaf Area Affected | Phytotoxicity at 7d: Percent Leaf Area Affected | Phytotoxicity at 10d: Percent Leaf Area Affected |
|---|---|---|---|
| Crop Oil Concentrate, 0.25% (v/v) | 0 A | 0 A | 0 A |
| NaSA 1600 mg/l + COC 0.25% | 11.3 B | 6.25 A | 5.5 BC |
| Keyplex 12.5 ml/l + COC 0.25% | 0 A | 2.5 A | 1.1 AB |
| Keyplex 60 ml/l + COC 0.25% | 0 A | 2 A | 1.1 AB |
| Paraquat 250 mg/l + COC 0.25% | 75 E | 96.5 D | 99 F |
| Paraquat 250 mg/l + NaSA 1600 mg/l + COC 0.25% | 15.5 C | 30.5 B | 20.8 E |
| Paraquat 250 mg/l + Keyplex 12.5 ml/l + COC 0.25% | 25 D | 30.5 B | 20.5 D |
| Paraquat 250 mg/l + Keyplex 60 ml/l + COC 0.25% | 1.5 A | 5.5 A | 10 C | n = 5 plants. Mean separation by Duncan's New Multipie Range Test (α = 0.05).

Example 10

The addition of the SAR inducer Ethephon to the spray solution safened the plants from paraquat herbicide damage on tobacco (Table 11). This result was observed regardless of pre-treatment with 1-MCP, an inhibitor of ethylene perception. The effect was observed throughout the course of the experiment. This table demonstrates that the observed affect is not limited to SAR inducers which modulate the SA-dependent pathway, but is observed with the ethylene-dependent pathway.

TABLE 11

Effect of Florel ® (Ethephon) spray on paraquat herbicidal activity against tobacco

| Treatment | Phytotoxicity at 4d post-spraying: Percent Leaf Area Affected | Phytotoxicity at 6d post-spraying: Percent Leaf Area Affected |
|---|---|---|
| Crop Oil Concentrate 0.25% (v/v) | 0 A | 0 A |
| Ethephon 1000 ul/l + COC 0.25% | 0 A | 0 A |
| Paraquat 187 mg/l + COC 0.25% | 95 C | 97.5 C |
| Paraquat 187 mg/l + Ethephon 1000 ul/l + COC 0.25% | 75 B | 65 B |

Florel ® is a 3.9% (w/v) solution of ethephon (2-choroethyl) phosphonic acid
n = 4 plants. Mean separation by Duncan's New Multiple Range Test (α = 0.05).

Example 11

The ability of SAR inducers to safen plant species from paraquat is broader than that observed with salicylic acid. One of the weed species tested, lambsquarter, showed limited or no protection from paraquat damage when salicylate acid was applied, but did show safening when BTH was tank mixed with paraquat (Table 12).

TABLE 12

Effect of Actigard (BTH) on paraquat herbicidal activity against lambsquarter (*Chenopodium album*)

| Treatment | Phytotoxicity at 2d: Percent Leaf Area Affected | Phytotoxicity at 4d: Percent Leaf Area Affected | Phytotoxicity at 7d: Percent Leaf Area Affected |
|---|---|---|---|
| Crop Oil Concentrate, 0.25% (v/v) | 0 A | 0 A | 0 A |
| NaSA 1600 mg/l + COC 0.25% | 17.5 AB | 16.25 A | 10 A |
| Actigard 187 mg/l + COC 0.25% | 0 A | 0 A | 0 A |
| Actigard 935 mg/l + COC 0.25% | 0 A | 0 A | 0 A |
| Paraquat 150 mg/l + COC 0.25% | 72.5 C | 72.5 BC | 72.5 BC |
| Paraquat 150 mg/l + NaSA 1600 mg/l + COC 0.25% | 73.75 C | 78.75 C | 85 C |
| Paraquat 150 mg/l + Actigard 187 mg/l + COC 0.25% | 47.5 BC | 46.25 B | 50 B |
| Paraquat 150 mg/l + Actigard 935 mg/l + COC 0.25% | 46.25 BC | 53.75 BC | 62.5 BC |

N = 5 plants. Mean separation by Duncan's New Multiple Range Test ($\alpha$ = 0.05).

One utility of this invention is the use of a salicylate or another SAR inducer to safen a crop plant to paraquat or another bipyridylium salt herbicide (PSI inhibitor). The use of salicylates or other SAR inducers to safen against PSI inhibitor herbicides may be employed commercially through the direct spray application of salicylates or other SAR inducers to crop and non-target species, application of salicylate or another SAR inducer in irrigation or hydroponic solutions, or seed treatments with a salicylate or another SAR inducer.

Another utility of this invention is to screen for new anti-stress compounds. For example, the efficacy of candidate anti-stress compounds could be assessed by determining their ability to reduce the herbicidal activity of a PSI inhibitor, such as paraquat. Typical candidate anti-stress compounds include, but are not limited to, free-radical quenchers and inducers of enzymes involved in free radical protection or other means of plant protection. These compounds could potentially be used to reduce a variety of plant stresses such as chilling injury, frost damage, postharvest disorders, salt stress, high light stress, water stress, pollutant stress such as that of ozone, senescence, or internal breakdown.

Another utility of this invention is to identify formulations or application methods that optimize the performance of known anti-stress compounds. For example, the efficacy of candidate formulations could be assessed by determining their ability to reduce the herbicidal activity of a PSI inhibitor, such as paraquat.

Another utility of this invention is to selectively safen plants by increasing endogenous defense levels. This could be accomplished through the use of elicitors which could raise endogenous plant defenses. In addition, safening of crop plants to PSI inhibitors, such as paraquat may be achieved through breeding or genetic engineering to produce a plant with enhanced resistance to pests or pathogens.

What is claimed is:

1. An herbicide composition comprising a photosystem I inhibitor and a salicylate or another systemically acquired resistance inducer.

2. An herbicide composition as in claim 1 wherein the photosystem I inhibitor is paraquat or diquat.

3. An herbicide composition as in claim 1 wherein the photosystem I inhibitor is from 99.999% to 0.001% of the composition and the salicylate or other systemically acquired resistance inducer is from 99.999% to 0.001% of the composition.

4. An herbicide composition as in claim 1 that is dissolved in water.

5. An herbicide composition as in claim 4 wherein the water is from 0.1% to 99.9% of the composition.

6. An herbicide composition as in claim 1 wherein the systemically acquired resistance inducer is Benzo(1,2,3)thiadiazole-7-carbothioic acid-S-methyl ester (BTH), or a biologically acceptable derivative or salt thereof.

7. An herbicide composition as in claim 1 wherein the systemically acquired resistance inducer is Harpin protein, or a biologically acceptable salt thereof.

8. An herbicide composition as in claim 1 wherein the systemically acquired resistance inducer is Keyplex 350-DP, or other Keyplex formulation thereof.

9. An herbicide composition as in claim 1 wherein the systemically acquired resistance inducer is 2-butyl-1,2-benzoisothiazole-3(2H)-one 1,1-dioxide(Probenazole), or a biologically acceptable derivative or salt thereof.

10. An herbicide composition as in claim 1 wherein the systemically acquired resistance inducer is an elicitor including fungal cell wall fragments, or an elicitor-based formulation thereof.

11. An herbicide composition as in claim 1 wherein the systemically acquired resistance inducer is ethylene, or any formulation which releases ethylene gas upon degradation thereof.

12. An herbicide composition as in claim 1 wherein the salicylate is salicylic acid or a biologically acceptable salt thereof.

13. An herbicide composition as in claim 1 wherein the salicylate is sodium salicylate.

14. A method for safening a crop plant against the herbicidal activity of a photosystem I inhibitor comprising adding to the inhibitor an effective amount of a systemically acquired resistance inducer.

15. A method for increasing the selectivity of an herbicide composition containing a photosystem I inhibitor comprising adding to the composition an effective amount of a systemically acquired resistance inducer.

* * * * *